United States Patent [19]

Murtiashaw

[11] Patent Number: 5,008,384
[45] Date of Patent: Apr. 16, 1991

[54] PROCESS FOR THE PRODUCTION OF O2,2'-ANHYDRO-1-(β-D-ARABINOFURANOSYL)THYMINE

[75] Inventor: Charles W. Murtiashaw, North Stonington, Conn.

[73] Assignee: Pfizer Inc., New York, N.Y.

[21] Appl. No.: 217,906

[22] Filed: Jul. 12, 1988

[51] Int. Cl.$^5$ .................... C07H 19/09; C07H 19/073
[52] U.S. Cl. ......................................... 536/23; 514/49
[58] Field of Search ................ 536/23; 514/269, 49, 514/50

[56] References Cited

U.S. PATENT DOCUMENTS

| | | | |
|---|---|---|---|
| 3,322,747 | 5/1967 | Shew et al. | 536/23 |
| 3,463,850 | 8/1969 | Shew et al. | 536/23 |
| 3,709,874 | 1/1973 | Moffatt et al. | 536/23 |
| 3,792,040 | 2/1974 | Moffatt et al. | 536/23 |
| 3,812,098 | 5/1974 | Moffatt et al. | 536/23 |
| 3,873,515 | 3/1975 | Sowa et al. | 536/23 |
| 3,920,630 | 11/1975 | Wechter et al. | 536/23 |

FOREIGN PATENT DOCUMENTS

63-6557  2/1988  Japan .

OTHER PUBLICATIONS

Reaction of Sugar-2-Amino-[1',2': 4,5] Oxazolines with substituted alkyl β-Halo and β-Alkoxyacrylates, Coll. Czech. Chem. Commun., 39, 1974, 3177.
5-Fluorouracil Derivatives VII[1] Tert Amine Promoted N-Glycosylation of Pyrimidines, Tet. Lett. 25, 1984, 5061.
2,2' Anhydropyrimidine Nucleosides, Novel Snythesis and Reaction, J. Org. Chem., 38, 1973, 593.
Nucleic acid components and their analogues CLVI Preparation of Enantiomeric 1-(α-Xylofuranosyl), 1--(α-Xylofuranosyl), 1-(α-Lyxofuranosyl) and 1-(-2-Deoxy-α-Lyxofuranosyl), Derivatives of Uracil and Cytosine Coll. Czech. Chem. Commun. 38 (1973), p. 423.
Rearrangement of Anhydropyrimidine Nucleosides in Liquid Hydrogen Fluoride, Mechanism, Scope, and Synthetic Studies, J. Org. Chem. 39, 1974, 3114.
March, J., 1977, Advanced Organic Chemistry, Mc Graw-Hill Book Co., New York, pp. 313, 343, 349.
Holy, A., (1973), Coll. Czech. Chem. Commun., vol. 38, pp. 423–427.
Ozaki et al., (1984), Tetrohedron Letters, vol. 25, No. 44, pp. 5061–5062.
Shannahoff et al., (1973), J. Org. Chem., vol. 38, No. 3, pp. 593–598.
Polazzi et al., (1974), J. Org. Chem., vol. 39, No. 21, pp 3114–3119.
Holy A., (1974), Coll. Czech. Chem. Commun., vol. 39, pp. 3177–3186.

*Primary Examiner*—Johnnie R. Brown
*Assistant Examiner*—Gary L. Kunz
*Attorney, Agent, or Firm*—Peter C. Richardson; Paul H. Ginsburg; Robert F. Sheyka

[57] ABSTRACT

In the disclosed process, an $O^2$, 2' anhydro-1-(β-D-arabinofuranosyl)thymine is formed by condensing a 2-amino-β-arabinofurano[1',2':4,5,]-2-oxazoline with a compound of the formula

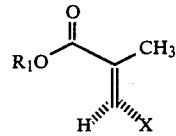

wherein $R_1$ is $C_1$–$C_4$ alkyl; X is halogen or $OR_2$, wherein $R_2$ is H, $C_1$–$C_4$ alkyl or phenyl; in the presence of a suitable solvent at about 0° C. to about 150° C. Catalytic agents such as dimethylaminopyridine and triethylamine may also be added to accelerate the reaction.

Protected intermediates of the anhydronucleosides and aminooxazolines are also disclosed.

14 Claims, No Drawings

PROCESS FOR THE PRODUCTION OF O2,2'-ANHYDRO-1-(β-D-ARABINOFURANOSYL)THYMINE

BACKGROUND OF THE INVENTION

Pyrimidine nucleosides are important antiviral agents. Increased attention has recently been focussed on these compounds with the FDA approval of 3'-azido2',3'-dideoxythymidine (AZT) as an effective treatment for Acquired Immunodeficiency Syndrome (AIDS). Since the synthesis of AZT utilizes the pyrimidine nucleoside β-thymidine as a starting material, new methods for the low-cost production of this synthetic intermediate are also becoming important. The present invention involves an expeditious route to the $O^2,2'$-anhydro-1(β-D-arabinofuranosyl)thymine nucleosides, a class of compounds easily converted to the β-thymidine derivatives. The synthesis of these anhydronucleosides is described in the following publications.

Japanese Kokai No. 81 49 398 laid open on May 2, 1981 refers to the synthesis of acylated arabinofuranosylcyclothymine compounds. The process of the Japanese Kokai requires that the iminoarabino[1', 2':4,5] oxazoline acid addition salt be acylated.

In an article appearing in J. Mol. Biol., 1970, 47, 537, the authors describe the use of a readily available amino-oxazoline carbohydrate derivative as a useful precursor to a variety of anhydronucleosides.

In an article appearing in Coll. Czechoslov. Chem. Comm., 1974, 39, 3177, the author reports the unsuccessful attempt to convert a 2-amino-β-D-arabinofuano[1', 2':4,5]-2-oxazoline into $O^2,2'$-anhydro-1-(β-D-arabinofuranosyl)thymine.

SUMMARY OF THE INVENTION

The present invention is directed to a process for the production of a compound of the formula:

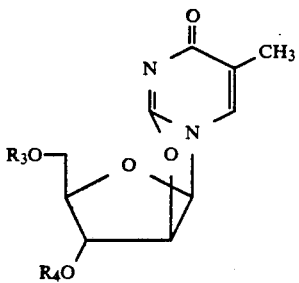

(I)

wherein $R_3$ is hydrogen, triphenylmethyl, or silyl which is substituted by three substituents selected from $C_1$–$C_6$ alkyl, phenyl, or combinations thereof, and $R_4$ is hydrogen, or silyl which is substituted by three substituents selected from $C_1$–$C_6$ alkyl, phenyl, or combinations thereof; comprising condensing a compound of the formula:

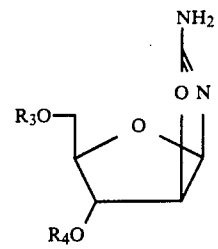

(II)

wherein $R_3$ is hydrogen, triphenylmethyl, or silyl which is substituted by three substituents selected from $C_1$–$C_6$ alkyl, phenyl, or combinations thereof, and $R_4$ is hydrogen, or silyl which is substituted by three substituents selected from $C_1$–$C_6$ alkyl, phenyl, or combinations thereof; with a compound of the formula:

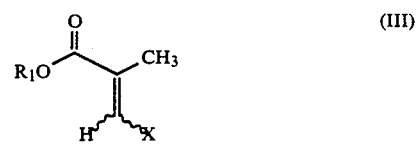

(III)

wherein $R_1$ is $C_1$–$C_4$ alkyl; X is halogen or $OR_2$, wherein $R_2$ is H, $C_1$–$C_4$ alkyl or phenyl; in the presence of a reaction-inert solvent at a temperature of 0° C. to about 150° C.

In a preferred embodiment, X is a halogen, preferably bromine.

In another preferred embodiment, $R_2$ is H,

In other preferred embodiments, basic catalysts can be added. These include the tertiary amines and inorganic salts. Preferred catalysts are dimethylaminopyridine, triethylamine, N-methylmorpholine, and combinations thereof.

The present invention is also directed to compounds of the formula:

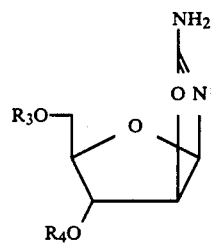

wherein $R_3$ is hydrogen, triphenylmethyl, or silyl substituted by three substituents selected from $C_1$–$C_6$ alkyl, phenyl, and combinations thereof, and $R_4$ is hydrogen, or silyl substituted by three substituents selected from $C_1$–$C_6$ alkyl, phenyl and combinations thereof, provided that when $R_3$ is hydrogen, $R_4$ is substituted silyl, and when $R_4$ is hydrogen, $R_3$ is triphenylmethyl or substituted silyl.

The present invention is also directed to compounds of the formula:

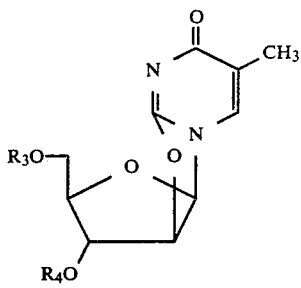

(I)

wherein $R_3$ is hydrogen, triphenylmethyl, or silyl which is substituted by three substituents selected from $C_1$–$C_6$ alkyl, phenyl, or combinations thereof, and $R_4$ is hydrogen, or silyl which is substituted by three substituents selected from $C_1$–$C_6$ alkyl, phenyl, and combinations thereof, provided that when $R_3$ is hydrogen, $R_4$ is substituted silyl, and when $R_4$ is hydrogen, $R_3$ is triphenylmethyl or substituted silyl.

DETAILED DESCRIPTION OF THE INVENTION

In the process of the present invention, one of the starting materials is a 2-amino-$\beta$-D-arabinofurano[1',2':4,5]-2-oxazoline of the formula:

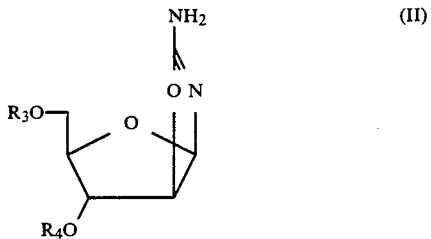

(II)

wherein $R_3$ is hydrogen, triphenylmethyl, or silyl which is substituted by three substituents selected from $C_1$–$C_6$ alkyl, phenyl, or combinations thereof, and $R_4$ is hydrogen or silyl which is substituted by three substituents selected from $C_1$–$C_6$ alkyl, phenyl, and combinations thereof. The 2-amino-$\beta$-D-arabinofurano[1',2',4,5]-oxazoline may be synthesized using the procedure described in Shannanhoff, D. H. and Sanchez, R. A.; J. Org. Chem 1973, 38, 593.

The other starting material of the process of the present invention is a compound of the formula:

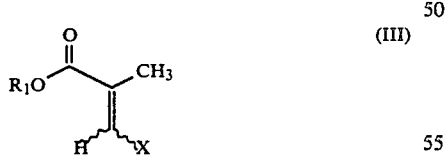

(III)

wherein $R_1$ is $C_1$–$C_4$ alkyl, X is halogen or $OR_2$ wherein $R_2$ is H, $C_1$–$C_4$ alkyl or phenyl, Compounds of formula III wherein X is halogen may be obtained from an acrylate ester by a sequence involving halogenation followed by dehydrohalogenation. This sequence of reactions is carried out under conventional conditions, (0° C., 24 hours, etc), for such reactions.

In a preferred embodiment, the compound of formula (III) is a 2-formyl propionate, it being readily appreciated by those skilled in the art that when $R_2$ is H, the compound of formula (III) can exist in the tautomeric form, in which case, formula (III) includes compounds such as

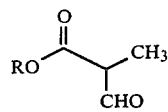

The process of the present invention comprises the reacting of a compound of the formula (II) with a of the formula (III) to yield the $O^2,2'$-anhydro-1-($\beta$-D-arabinofuranosyl)thymine of formula (I). This process is preferably carried out at a temperature of from about 0° C. to about 150° C., preferably 20° to 80° C., in the presence of a reaction-inert solvent. Preferred solvents are organic solvents such as $C_1$–$C_4$ alkanols, preferably methanol, and other suitable solvents including dimethyl sulfoxide, dimethylformamide, dimethylacetamide, acetone, etc. Water may also be used as a solvent. Although the preferred embodiment employs equimolar amounts of compounds II and III, an excess of either reagent may be used.

In addition, the reaction between compounds of formula (II) and those of formula (III) may also be conducted in the presence of an appropriate catalyst. One particularly preferred catalyst is dimethylaminopyridine. Other preferred catalysts include triethylamine, pyridine, sodium hydroxide, diisopropylethylamine and N-methylmorpholine.

In the foregoing reaction between the compounds of formula (II) and formula (III), the pressure is not critical. Generally, the reaction is conducted at a pressure of from about 0.5 to about 2.0 atmospheres, preferably at ambient pressure, (i.e. about one atmosphere).

It will also be appreciated by those skilled in the art that the mono-protected 2-amino-oxazoline starting material of formula II also forms a part of the present invention. This compound has the formula:

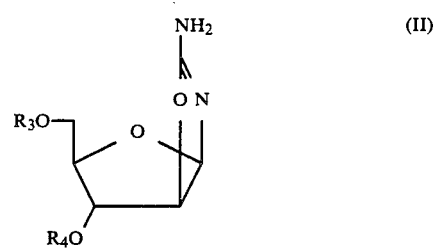

(II)

wherein $R_3$ is hydrogen, triphenylmethyl, or silyl which is substituted by three substituents selected from $C_1$–$C_6$ alkyl, phenyl, or combinations thereof, and $R_4$ is hydrogen, or silyl which is substituted by three substituents selected from $C_1$–$C_6$ alkyl, phenyl, or combinations thereof, provided that when $R_3$ is hydrogen, $R_4$ is substituted silyl, and when $R_4$ is hydrogen, $R_3$ is triphenylmethyl or substituted silyl.

Similarly, the mono protected anhydronucleosides also form a part of the present invention. These compounds have the formula

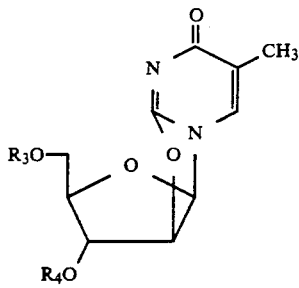

wherein R₃ is hydrogen, triphenylmethyl, or silyl which is substituted by three substituents selected from $C_1$–$C_6$ alkyl, phenyl, or combinations thereof, R₄ is hydrogen or silyl which is substituted by three substituents selected from $C_1$–$C_6$ alkyl, phenyl, and combinations thereof, provided that when R₃ is hydrogen, R₄ is substituted silyl, and when R₄ is hydrogen, R₃ is triphenylmethyl or substituted silyl.

The following scheme illustrates the general scheme of placing and removing the protecting groups on either the amino-oxazoline or anhydronucleoside. (TBS=t-butyldimethylsilyl)

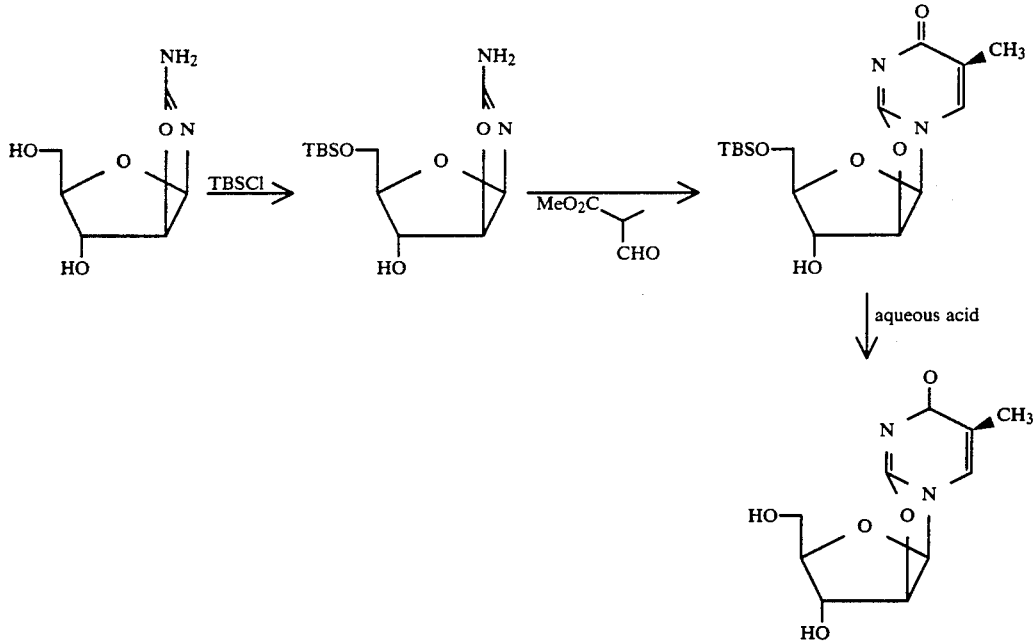

Once the $O^2,2'$-anhydro-1-($\beta$-D-arabinofuranosyl)thymine is produced, it may be converted to $\beta$-thymidine via the following route:

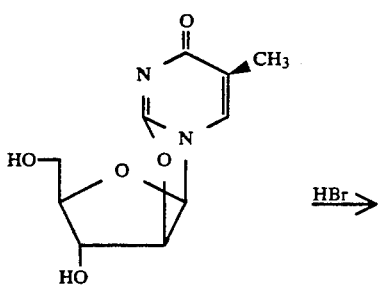

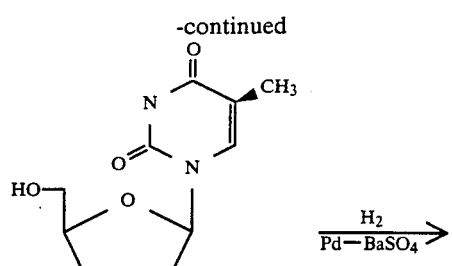

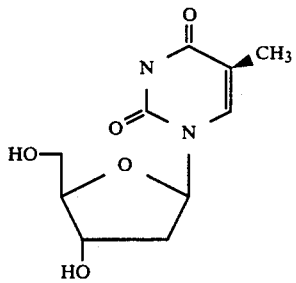

The removal of the bromine may be accomplished by a variety of methods including reductions by hydrogenation and trialkyl tin hydrides.

Having described the invention in general terms, reference is now made to specific examples. It is to be understood that these examples are not to limit the present invention, the scope of which is determined by the appended claims.

EXAMPLE 1

Synthesis of methyl 2-formylpropionate

In a one liter three neck flask was placed 90 ml tetrahydrofuran and 60.72 g (0.6 mol) of diisopropylamine. The solution was cooled to −78° C. and then treated with the dropwise addition of 0.229 liters of 2.4M n-buLi solution (hexanes). After stirring at −78° C for 30 min., 44.50 g (0.50 mol) of methyl propionate was slowly added and then allowed to stir an additional 15 minutes before 45.04 g (0.75 mol) of methyl formate was added in a dropwise fashion. The resulting yellow suspension, after slowly warming to room temperature overnight, was cooled to 0° C. and carefully quenched with 250 ml of 4.4M $H_2SO_4$. The reaction mixture was poured into a separatory funnel and extracted twice with ethyl acetate. The organic layers were then combined, dried over magnesium sulfate and stripped to provide 47.86 g (82.4%) of yellow oil. Distillation at 47 mm Hg gave 23.88 g methyl 2-formylpropionate as the major fraction.

EXAMPLE 2

Synthesis of methyl 3-bromomethacrylate (a) After cooling to 0° C., 25.03 g (0.25 mol) of methyl methacrylate was treated with the dropwise addition of 12.9 ml (0.25 mol) of bromine. The deep red reaction mixture was allowed to warm to room temperature, stirred for 24 hours, and was then transferred to a separatory funnel where it was washed once with 50 ml of saturated sodium bisulfite. The aqueous layer was extracted once with methylene chloride and the organic layers combined. The resulting organic solution was dried over sodium sulfate and concentrated in vacuo, providing methyl 2,3-dibromo-2-methylpropionate as a clear, colorless oil (64.7 g, 99.7%).

(b) To a solution of 30 g (0.115 mmol) of methyl 2,3-dibromo-2-methylpropionate, synthesized in step (a) above, dissolved in 23 ml of methanol was added a solution of 4.61 g of sodium methoxide (0.085 mol) in 46 ml of methanol over 30 minutes via a dropping funnel. After stirring for 16 hours, the clear solution was evaporated, redissolved in $H_2O$ and extracted twice with ethyl acetate. The combined organic layers were dried over sodium sulfate, concentrated in vacuo and then distilled at 25 mm of Hg. The desired methyl 3-bromomethacrylate (8.5 g, 56% based on sodium methoxide) was obtained as the major fraction, boiling at 70°–77° C.

EXAMPLE 3

Synthesis of 2-amino-β-D-arabinofurano[1',2':4,5]-2-oxazoline

The procedure used was that of Shannahoff, D. H. and Sanchez, R. A.; J. Org. Chem. 1973, 38, 593.

A concentrated ammonia solution (5.0 ml) and crystalline cyanamid (8.4 g, 0.20 ml) were added to a stirred slurry of D-arabinose (15.0 g, 0.10 mmol) in 50 ml of methanol. The mixture was stirred for 4 hr at 40°–45° C. and then chilled in an ice bath. After filtering, washing with cold methanol and air drying, the white powder weighed 14.1 g. (81%) and melted at 175°–176°. The pKa in water was determined titrimetrically to be 6.52.

EXAMPLE 4

Synthesis of $O^2$,2'-anhydro-1-(β-D-arabinofuranosyl)thymine

A suspension of 0.087 g (0.5 mmol) of the 2-amino-β-D-arabinofurano[1',2':4,5]-2-oxazoline of Example 3, 0.090 g (0.5 mmol) methyl 3-bromomethacrylate, 6 mg (0.05 mmol) 4-dimethylaminopyridine, and 1 ml triethylamine was heated for 4 days at 80° C. After diluting with methanol, the solids were filtered off and discarded. The final product was isolated by chromatography from silica gel to give 3 mg of $O^2$,2'-anhydro-1-(β-D-arabinofuranosyl)thymine as an oil. NMR(250 MHz; $D_6$DDMSO)δ7.75 (d, 1H, J=1.33 Hz), 6.29 (d, 1H, J=5.75 Hz), 5.88 (d, 1H, J=4.52 Hz), 5.15 (d, 1H, J=5.75 Hz), 4.97 (t, 1H, J=5.31 Hz), 4.37 (br, s, 1H), 4.06 (m, 1H), 3.22 (m, 2H), 1.79 (d, 3H, J=0.9 Hz).

EXAMPLE 5

Synthesis of $O^2$,2'-anhydro-1-(β-D-arabinofuranosyl)thymine

A solution of 0.17 g (1.0 mmol) 2-amino-β-D-arabinofurano[1',2':4,5]-2-oxazoline and 0.130 g (1.0 mmol) methyl 3-methoxymethacrylate in 1 ml dimethylsulfoxide was heated for four days at 80° C. After removing the dimethylsulfoxide under reduced pressure, the $O^2$,2'-anhydro-1-(β-D-arabinofuranosyl)thymine was isolated by silica gel chromatography as an oil (38 mg, (32%)) containing material identical to that prepared in Example 4.

EXAMPLE 6

Synthesis of $O^2$,2'-anhydro-1-(β-D-arabinofuranosyl)thymine

In a small vial equipped with a magnetic stir bar was combined 0.5 ml of water, 0.5 ml of methanol, 65 mg (0.5 mmol) of ethyl 2-formylpropionate and 87 mg (0.5 mmol) of 2-amino-β-D-arabinofurano[1',2':4,5]-2-oxazoline. The resulting stirrable suspension was then treated with 50 mg of triethylamine and allowed to stir at room temperature for 24 hours followed by heating at 60° C. for another 24 hour period. The reaction product was then concentrated to dryness and purified by thin layer chromatography (3:1 methylene chloride: ethanol) to yield 10 mg (8%) of product. NMR and MS spectral analysis showed material which was identical to that prepared in Example 4.

EXAMPLE 7

Synthesis of $O^2$,2'-anhydro-1-(β-D-arabinofuranosyl)thymine

A suspension of 2.0 g of 2-amino-β-D-arabinofurano[1',2': 4,5]-2-oxazoline (0.001 mol) and 2.0 g of methyl formylpropionate (0.017 mol) in 23 ml of water was adjusted to pH 8.1 using 2.0M NaOH. After 48 hr the resulting clear solution was concentrated in vacuo and purified by column chromatography (70–230 mesh silica gel, 3:1 methylene chloride: ethanol eluent). The clear fractions were condensed by rotary evaporator to yield 1.17 g (42%) of the $O^2$,2'-anhydro-1-[β-D-arabinofuranosyl)thymine as an off-white solid. NMR and MS spectral analysis showed material which was identical to that prepared in example 4.

EXAMPLE 8

2'-Bromothymidine

A mixture of 0.43 g. (1.8 mmoles) of $O^2$,2'-anhydro1-(β-D-arabinofuranosyl)thymine in 10–15 ml. of trifluoroacetic acid which had been saturated with dry hydrogen bromide at 0° was heated in a stainless steel container at 33°–37° for 48 hr. The orange solution was reduced in volume in vacuo, leaving a sirup. This was triturated well with petroleum ether, the petroleum ether was removed, and the residue was crystallized from ethanol to which a small amount of petroleum ether had been added to yield the title product as small colorless needles, mp. 186°–189 ° dec., $[\alpha]^{23}D$ −4° (c 0.6 water), 0.23 g. (40%).

Anal. Calcd for $C_{10}H_{13}BrN_2O_5$: C, 37.40; H, 4.08; Br, 24.88; N, 8.72. Found: C, 37.42; H, 4.47; Br, 25.08; N, 8.82.

EXAMPLE 9

Conversion of 2'-bromothymidine to β-thymidine

To a solution of 55 mg (0.173 mmol) of 2-bromothymidine in 1.5 ml of benzene was added 150 mg of tributyltin hydride via syringe. A crystal of azobisiobutyronitrile was then added and the solution was heated at reflux for 30 minutes. After removal of the solvent and chromatography, β-thymidine was obtained as a white solid in 95% yield.

EXAMPLE 10

Conversion of $O^2,2'$-anhydro-1(β-D-arabinofuranosyl)thymine to 2'-bromo-3',5'-diacetylthymine To a solution of 200 mg (0.083 mmol) of $O^2,2'$-anhydro-1-(β-D-arabinofuranosyl)thymine in 4.53 ml of ethyl acetate and 0.68 ml of dimethylformamide was added 0.185 ml (2.5 mmol) of acetyl bromide. The resulting solution was heated at reflux for 2 hours and then concentrated on the rotary evaporator. Chromatography of the residue provided 330 mg. (97%) of the 2'-bromo-3',5'-diacetylthymidine as a clear oil. $R_f$ 0.53 (EtOAc); $^1$H NMR (300 MHz, CDCl$_3$)δ 9.91 (s, 1H), 7.18 (s, 1H), 6.18 (d, 1H, J=6.1 Hz), 5.12 (m, 1H), 4.52 (t, 1H, J=5.7 Hz), 2.13 (s, 3H), 2.10 (s, 3H), 1.90 (s, 1H); $^{13}$C NMR (CDCl$_3$) 170.19, 169.79, 163.87, 150.50, 134.71, 111.85, 90.33, 80.00, 77.15, 76.73, 71.06, 60.40, 48.14, 20.81, 20.63, 12.66. The resultant product can be converted to β-thymidine using the procedure of Example 9.

EXAMPLE 11

Synthesis of 5'-t-butyldimethylsiloxy-2-amino-β-D-arabinofurano[1',2':4,5]-2-oxazoline To a cooled (0° C.) solution of amino-oxazoline (10 g, 0.057 mol) and imidazole (5.87 g, 0,086 mol) in DMF (100 ml) was added 8.66 g (0.057 mol) of t-butyldimethylsilyl chloride. The initially formed suspension was allowed to slowly warm to room temperature and continued stirring for 15 hours, at which point a clear, light yellow solution was obtained. The reaction mixture was then poured into 1 L of 2% Na$_2$CO$_3$, filtered, and the solid material washed with water. The resulting white solid was dissolved in ethyl acetate dried over MgSO$_4$, filtered and concentrated to 8.5 g of white solid which was recrystallized from 20 ml of hot EtOAc to provide 4.34 g (26%) of the desired mono-protected amino-oxazoline. m.p. 165°–166° C. $^1$H NMR (300 MHz, CDdCL$_3$)δ7.20 (s, 3H), 5.82 (d, 1H), 4.72 (dd, 1H), 4.21 (m, 1H), 3.79 (cm, 2H), 3.40 (t, 1H), 0.83 (s, 9H), 0.10 (s, 6H).

EXAMPLE 12

Synthesis of 5'-t'butyldimethylsiloxy-$O^2,2'$-anhydro-1-(β-D-arabinofuranosyl)thymine A benzene solution (5.0 ml) of 300 mg of 5'-t-butyldimethylsiloxy-2-amino-βD-arabinofurano[1',2':4,5]-2-oxazoline (1.04 mmol) and 181 mg of methyl 2-formylpropionate was heated for 1 hour at reflux in a flask equipped with a Dean-Stark trap and condenser. After evaporation of the solvent, the resulting oil was chromatographed on silica gel (70–230 mesh, 6:1 CH$_2$Cl$_2$:ethanol as eluent) to provide 170 mg (46%) of the desired 5'-t-butyldimethylsiloxy-$O^2,2'$-anhydro-1-(β-D-arabinofuranosyl)thymine as a slightly impure oil: $R_f$ 0.65 (3:1 CHCl$_3$:MeOH); $^1$H NMR (300 MHz, CDCl$_3$)δ 7.3 (s, 1H), 6.27 (d, 1H, J=5.4 Hz), 5.47 (d, 1H, 5.4 Hz), 4.61 (m, 1H), 4.39 (m, 1H), 3.57 (m, 2H), 1.94 (s, 3H), 0.81 (s, 9H), −0.02 (s, 3H), −0.03 (s, 3H).

EXAMPLE 13

Synthesis of 3',5'-di-t-butyldimethylsiloxy-$O^2,2'$-anhydro-1-(δ-D-arabinofuranosyl)thymine A benzene solution (5.0 ml) of 300 mg of 3',5'-di-t-butyldimethylsiloxy-2-amino-β-D-arabinofurano[1',2':4,5]-2-oxazoline (1.04 mmol) and 130 mg of methyl-2-formylpropionate was heated for 1 hour at reflux in a flask equipped with a Dean-Stark trap and condenser. Afer evaporation of the solvent, the resulting oil was chromatographed on silica gel (70–230 mesh. EtOAc as eluent) to provide 120 mg (26%) of the desired 3',5'-di-t-butyldimethylsiloxy-$O^2,2'$-anhydro-1-(β-D-arabinofuranosyl)thymine as a colorless oil: oil: $R_f$ 0.26 (EtOAc); $^1$H NMR (300 MHz, CDCl$_3$) delta 7.21 (s, 1H), 6.12 (d, 1H, J=8.0), 5.08 (d, 1H, J=8.0), 4.61 (s, 1H), 4.12 (m, 1H), 3.3–3.6 (cm, 1.90 (s, 3H), 0.92 (s, 9H), 0.85 (s, 9H), 0.17 (s, 3H), 0.14 (s, 3H), 0.0 (s, 3H), −0.02 (s, 3H).

What is claimed is:

1. A process for the production of a compound of the formula:

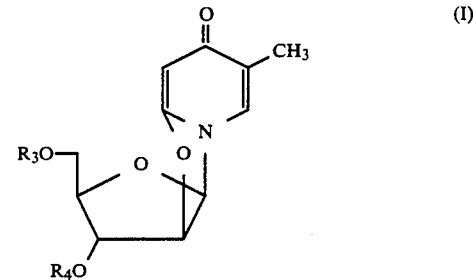

wherein $R_3$ is selected from the group consisting of hydrogen, triphenylmethyl or silyl which is substituted by three substituents selected from the group consisting of $C_1$–$C_6$ alkyl or phenyl and $R_4$ is selected from the group consisting of hydrogen, or silyl which is substituted by three substituents selected from the group consisting of $C_1$–$C_6$ alkyl or phenyl; comprising condensing a compound of the formula:

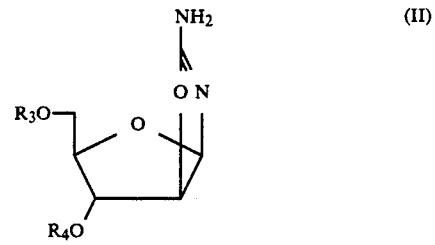

wherein $R_3$ is selected from the group consisting of hydrogen, triphenylmethyl, or silyl which is substituted by three substituents selected from the group consisting of $C_1$–$C_6$ alkyl or phenyl and $R_4$ is selected from the group consisting of hydrogen, or silyl which is substituted by three substituents selected from the group consisting of $C_1$–$C_6$ alkyl or phenyl with a compound of the formula:

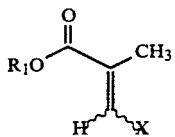 (III)

wherein $R_1$ is selected from the group consisting of $C_1$–$C_4$ alkyl; X is selected from the group consisting of halogen, or $OR_2$, wherein $R_2$ is selected from the group consisting of H, $C_1$–$C_4$ alkyl or phenyl; in the presence of a reaction-inert solvent at a temperature of from about 0° to about 150° C.

2. The process of claim 1 wherein $R_1$ is $C_1$–$C_4$ alkyl.
3. The process of claim 2 wherein $R_1$ is methyl.
4. The process of claim 1 wherein X is halogen.
5. The process of claim 4 wherein X is bromo.
6. The process of claim 3 wherein X is OH.
7. The process of claim 1 wherein R and $R_4$ are hydrogen.
8. The process of claim 1 wherein $R_3$ is t-butyldimethylsilyl and $R_4$ is hydrogen.
9. The process of claim 1 further comprising the inclusion of an amine catalyst.
10. The process of claim 9 wherein said catalyst is a tertiary amine.
11. The process of claim 10 wherein said tertiary amine is triethylamine.
12. The process of claim 9 wherein said catalyst is dimethylaminopyridine.
13. The process of claim 1 carried out at 80° C.
14. The process of claim 3 carried out at 80° C.

* * * * *